United States Patent
Brown et al.

(10) Patent No.: US 10,772,532 B2
(45) Date of Patent: Sep. 15, 2020

(54) REAL-TIME AUTOMATIC REGISTRATION FEEDBACK

(71) Applicant: Covidien LP, Mansfield, MA (US)

(72) Inventors: Andrew E. Brown, St. Paul, MN (US); Elad D. Lachmanovich, Modiin (IL); Eyal Klein, Herzliya (IL); Oren P. Weingarten, Hod-Hasharon (IL); Alexander Y. Nepomniashchy, Hertzliya (IL)

(73) Assignee: COVIDIEN LP, Mansfield, MA (US)

( * ) Notice: Subject to any disclaimer, the term of this patent is extended or adjusted under 35 U.S.C. 154(b) by 465 days.

(21) Appl. No.: 14/790,581

(22) Filed: Jul. 2, 2015

(65) Prior Publication Data
US 2016/0000356 A1 Jan. 7, 2016

Related U.S. Application Data

(60) Provisional application No. 62/020,220, filed on Jul. 2, 2014.

(51) Int. Cl.
*A61B 5/06* (2006.01)
*A61B 1/267* (2006.01)
(Continued)

(52) U.S. Cl.
CPC .......... *A61B 5/066* (2013.01); *A61B 1/00045* (2013.01); *A61B 1/04* (2013.01);
(Continued)

(58) Field of Classification Search
CPC ............................. A61B 5/06; A61B 19/5244
See application file for complete search history.

(56) References Cited

U.S. PATENT DOCUMENTS

| | | |
|---|---|---|
| 5,592,939 A | 1/1997 | Martinelli |
| 5,611,025 A | 3/1997 | Lorensen et al. |

(Continued)

FOREIGN PATENT DOCUMENTS

| | | |
|---|---|---|
| EP | 2253287 A2 | 11/2010 |
| JP | 2002153443 A | 5/2002 |
| JP | 2007503893 A | 3/2007 |
| JP | 2010510815 A | 4/2010 |
| JP | 2012527286 A | 11/2012 |

(Continued)

OTHER PUBLICATIONS

Extended European Search Report for application No. 15814452.7 dated Jan. 25, 2018 (7 pages).

(Continued)

*Primary Examiner* — Hien N Nguyen

(57) ABSTRACT

A method of registering a luminal network to a 3D model of the luminal network with real-time feedback is disclosed, including generating the 3D model of the luminal network based on images of the luminal network, generating an electromagnetic field about the luminal network, inserting a location sensor into the electromagnetic field, tracking the location of the sensor within the luminal network, comparing the tracked locations of the sensor with sensors located outside of the luminal network and the portions of the 3D model representative of open space, and presenting on a user interface an indication of which portions of the luminal network have been sufficiently traversed by the sensor to register that portion of the luminal network to the 3D model.

15 Claims, 11 Drawing Sheets

(51) Int. Cl.

| | | |
|---|---|---|
| *A61B 1/04* | (2006.01) | |
| *A61B 1/00* | (2006.01) | |
| *A61B 5/08* | (2006.01) | |
| *A61B 5/00* | (2006.01) | |
| *A61B 34/20* | (2016.01) | |
| *A61B 17/00* | (2006.01) | |
| *A61B 90/00* | (2016.01) | |
| *A61B 34/00* | (2016.01) | |
| *A61B 34/10* | (2016.01) | |

(52) U.S. Cl.
CPC ............ *A61B 1/2676* (2013.01); *A61B 5/062* (2013.01); *A61B 5/064* (2013.01); *A61B 5/0803* (2013.01); *A61B 5/7425* (2013.01); *A61B 2017/00809* (2013.01); *A61B 2034/105* (2016.02); *A61B 2034/2051* (2016.02); *A61B 2034/252* (2016.02); *A61B 2090/365* (2016.02)

(56) References Cited

U.S. PATENT DOCUMENTS

| | | |
|---|---|---|
| 5,676,673 A | 10/1997 | Ferre et al. |
| 5,697,377 A | 12/1997 | Wittkampf |
| 5,699,799 A | 12/1997 | Xu et al. |
| 5,715,836 A | 2/1998 | Kliegis et al. |
| 5,729,129 A | 3/1998 | Acker |
| 5,752,513 A | 5/1998 | Acker et al. |
| 5,782,762 A | 7/1998 | Vining |
| 5,881,124 A | 3/1999 | Giger et al. |
| 5,891,030 A | 4/1999 | Johnson et al. |
| 5,913,820 A | 6/1999 | Bladen et al. |
| 5,920,319 A | 7/1999 | Vining et al. |
| 5,967,980 A | 10/1999 | Ferre et al. |
| 5,971,767 A | 10/1999 | Kaufman et al. |
| 5,987,960 A | 11/1999 | Messner et al. |
| 6,019,725 A | 2/2000 | Vesely et al. |
| 6,047,080 A | 4/2000 | Chen et al. |
| 6,083,162 A | 7/2000 | Vining |
| 6,138,045 A | 10/2000 | Kupinski et al. |
| 6,151,404 A | 11/2000 | Pieper |
| 6,167,296 A | 12/2000 | Shahidi |
| 6,181,348 B1 | 1/2001 | Geiger |
| 6,201,387 B1 | 3/2001 | Govari |
| 6,233,476 B1 | 5/2001 | Strommer et al. |
| 6,246,784 B1 | 6/2001 | Summers et al. |
| 6,266,551 B1 | 7/2001 | Osadchy et al. |
| 6,332,089 B1 | 12/2001 | Acker et al. |
| 6,346,940 B1 | 2/2002 | Fukunaga |
| 6,366,800 B1 | 4/2002 | Vining et al. |
| 6,381,485 B1 | 4/2002 | Hunter et al. |
| 6,387,092 B1 | 5/2002 | Burnside et al. |
| 6,466,815 B1 | 10/2002 | Saito et al. |
| 6,496,188 B1 | 12/2002 | Deschamps et al. |
| 6,501,848 B1 | 12/2002 | Carroll et al. |
| 6,501,981 B1 | 12/2002 | Schweikard et al. |
| 6,505,065 B1 | 1/2003 | Yanof et al. |
| 6,522,907 B1 | 2/2003 | Bladen et al. |
| 6,526,162 B2 | 2/2003 | Asano et al. |
| 6,535,756 B1 | 3/2003 | Simon et al. |
| 6,578,579 B2 | 6/2003 | Burnside et al. |
| 6,584,174 B2 | 6/2003 | Schubert et al. |
| 6,603,868 B1 | 8/2003 | Ludwig et al. |
| 6,611,793 B1 | 8/2003 | Burnside et al. |
| 6,650,927 B1 | 11/2003 | Keidar |
| 6,651,669 B1 | 11/2003 | Burnside |
| 6,694,163 B1 | 2/2004 | Vining |
| 6,757,557 B1 | 6/2004 | Bladen et al. |
| 6,783,523 B2 | 8/2004 | Qin et al. |
| 6,792,390 B1 | 9/2004 | Burnside et al. |
| 6,829,379 B1 | 12/2004 | Knoplioch et al. |
| 6,850,794 B2 | 2/2005 | Shahidi |
| 6,892,090 B2 | 5/2005 | Verard et al. |
| 6,898,263 B2 | 5/2005 | Avinash et al. |
| 6,909,913 B2 | 6/2005 | Vining |
| 6,920,347 B2 | 7/2005 | Simon et al. |
| 6,925,200 B2 | 8/2005 | Wood et al. |
| 7,006,677 B2 | 2/2006 | Manjeshwar et al. |
| 7,072,501 B2 | 7/2006 | Wood et al. |
| 7,085,400 B1 | 8/2006 | Holsing et al. |
| 7,096,148 B2 | 8/2006 | Anderson et al. |
| 7,149,564 B2 | 12/2006 | Vining et al. |
| 7,167,180 B1 | 1/2007 | Shibolet |
| 7,174,202 B2 | 2/2007 | Bladen et al. |
| 7,179,220 B2 | 2/2007 | Kukuk |
| 7,236,558 B2 | 6/2007 | Saito et al. |
| 7,301,332 B2 | 11/2007 | Govari et al. |
| 7,315,639 B2 | 1/2008 | Kuhnigk |
| 7,324,104 B1 | 1/2008 | Bitter et al. |
| 7,336,809 B2 | 2/2008 | Zeng et al. |
| 7,397,937 B2 | 7/2008 | Schneider et al. |
| 7,428,334 B2 | 9/2008 | Schoisswohl et al. |
| 7,452,357 B2 | 11/2008 | Vlegele et al. |
| 7,505,809 B2 | 3/2009 | Strommer et al. |
| 7,517,320 B2 | 4/2009 | Wibowo et al. |
| 7,518,619 B2 | 4/2009 | Stoval, III et al. |
| 7,630,752 B2 | 12/2009 | Viswanathan |
| 7,630,753 B2 | 12/2009 | Simon et al. |
| 7,659,912 B2 | 2/2010 | Akimoto et al. |
| 7,702,153 B2 | 4/2010 | Hong et al. |
| 7,751,865 B2 | 7/2010 | Jascob et al. |
| 7,756,316 B2 | 7/2010 | Odry et al. |
| 7,788,060 B2 | 8/2010 | Schneider |
| 7,792,565 B2 | 9/2010 | Vining |
| 7,805,269 B2 | 9/2010 | Glossop |
| 7,809,176 B2 | 10/2010 | Gundel |
| 7,811,294 B2 | 10/2010 | Strommer et al. |
| 7,822,461 B2 | 10/2010 | Geiger et al. |
| 7,901,348 B2 | 3/2011 | Soper et al. |
| 7,907,772 B2 | 3/2011 | Wang et al. |
| 7,929,014 B2 | 4/2011 | Akimoto et al. |
| 7,951,070 B2 | 5/2011 | Ozaki et al. |
| 7,969,142 B2 | 6/2011 | Krueger et al. |
| 7,985,187 B2 | 7/2011 | Wibowo et al. |
| 8,009,891 B2 | 8/2011 | de Vaan |
| 8,049,777 B2 | 11/2011 | Akimoto et al. |
| 8,055,323 B2 | 11/2011 | Sawyer |
| 8,102,416 B2 | 1/2012 | Ito et al. |
| 8,126,241 B2 | 2/2012 | Zarkh et al. |
| 8,131,344 B2 | 3/2012 | Strommer et al. |
| 8,170,328 B2 | 5/2012 | Masumoto et al. |
| 8,199,981 B2 | 6/2012 | Koptenko et al. |
| 8,200,314 B2 | 6/2012 | Bladen et al. |
| 8,202,213 B2 | 6/2012 | Ito et al. |
| 8,208,708 B2 | 6/2012 | Homan et al. |
| 8,219,179 B2 | 7/2012 | Ganatra et al. |
| 8,257,346 B2 | 9/2012 | Qin et al. |
| 8,267,927 B2 | 9/2012 | Dalal et al. |
| 8,290,228 B2 | 10/2012 | Cohen et al. |
| 8,298,135 B2 | 10/2012 | Ito et al. |
| 8,391,952 B2 | 3/2013 | Anderson |
| 8,417,009 B2 | 4/2013 | Mizuno |
| 8,494,612 B2 | 7/2013 | Vetter et al. |
| 8,509,877 B2 | 8/2013 | Mori et al. |
| 8,672,836 B2 | 3/2014 | Higgins et al. |
| 8,682,045 B2 | 3/2014 | Vining et al. |
| 8,696,549 B2 | 4/2014 | Holsing et al. |
| 8,698,806 B2 | 4/2014 | Kunert et al. |
| 8,700,132 B2 | 4/2014 | Ganatra et al. |
| 8,706,193 B2 | 4/2014 | Govari et al. |
| 8,709,034 B2 | 4/2014 | Keast et al. |
| 8,730,237 B2 | 5/2014 | Ruijters et al. |
| 8,768,029 B2 | 7/2014 | Helm et al. |
| 8,784,400 B2 | 7/2014 | Roschak |
| 8,798,227 B2 | 8/2014 | Tsukagoshi et al. |
| 8,798,339 B2 | 8/2014 | Mielekamp et al. |
| 8,801,601 B2 | 8/2014 | Prisco et al. |
| 8,819,591 B2 | 8/2014 | Wang et al. |
| 8,862,204 B2 | 10/2014 | Sobe et al. |
| 2005/0267353 A1* | 12/2005 | Marquart ............ A61B 17/154 600/411 |
| 2008/0118135 A1* | 5/2008 | Averbuch ............ G06T 7/0012 382/131 |
| 2008/0183073 A1 | 7/2008 | Higgins et al. |

(56) References Cited

U.S. PATENT DOCUMENTS

| | | |
|---|---|---|
| 2009/0012390 A1 | 1/2009 | Pescatore et al. |
| 2009/0030306 A1 | 1/2009 | Miyoshi et al. |
| 2009/0227861 A1* | 9/2009 | Ganatra ............... A61B 34/20 600/424 |
| 2010/0034449 A1* | 2/2010 | Averbuch ............... A61B 5/06 382/131 |
| 2010/0310146 A1 | 12/2010 | Higgins et al. |
| 2010/0312094 A1 | 12/2010 | Guttman et al. |
| 2011/0237897 A1 | 9/2011 | Gilboa |
| 2011/0251607 A1 | 10/2011 | Kruecker et al. |
| 2012/0203065 A1 | 8/2012 | Higgins et al. |
| 2012/0249546 A1 | 10/2012 | Tschirren et al. |
| 2012/0280135 A1 | 11/2012 | Bal |
| 2012/0287238 A1 | 11/2012 | Onishi et al. |
| 2013/0165854 A1 | 6/2013 | Sandhu et al. |
| 2013/0281821 A1 | 10/2013 | Liu et al. |
| 2014/0343416 A1* | 11/2014 | Panescu ............... A61B 34/30 600/431 |
| 2015/0138186 A1* | 5/2015 | Carrell ............... F24C 15/2021 345/419 |

FOREIGN PATENT DOCUMENTS

| | | |
|---|---|---|
| WO | 03086498 A2 | 10/2003 |
| WO | 2005058137 A2 | 6/2005 |
| WO | 2008095068 A1 | 8/2008 |
| WO | 2008125910 A2 | 10/2008 |
| WO | 2011102012 A1 | 8/2011 |
| WO | 2013145010 A1 | 10/2013 |
| WO | 2014025550 A1 | 2/2014 |
| WO | 2014028394 A1 | 2/2014 |
| WO | 2014058838 A1 | 4/2014 |

OTHER PUBLICATIONS

Japanese Office Action issued in corresponding Appl. No. JP 2016-575071, dated Nov. 26, 2018, together with English language translation (7 pages).

Australian Examination Report issued in correspodning Appl. No. AU 2015283946 dated Mar. 1, 2019 (3 pages).

European Examination Report issued in corresponding Appl. No. EP 15 814 452.7 dated Dec. 9, 2019 (4 pages).

* cited by examiner

REAL-TIME AUTOMATIC REGISTRATION FEEDBACK

CROSS REFERENCE TO RELATED APPLICATIONS

The present application claims the benefit of and priority to U.S. Provisional Patent Application Ser. No. 62/020,220 filed on Jul. 2, 2014, the entire contents of which are incorporated herein by reference.

BACKGROUND

Technical Field

The present disclosure relates to bronchial registration and, more particularly, to devices, systems, and methods for automatically registering a bronchial tree model with a patient's real bronchial tree.

Description of Related Art

A common device for inspecting the airway of a patient is a bronchoscope. Typically, the bronchoscope is inserted into a patient's airways through the patient's nose or mouth and can extend into the lungs of the patient. A typical bronchoscope includes an elongated flexible tube having an illumination assembly for illuminating the region distal to the bronchoscope's tip, an imaging assembly for providing a video image from the bronchoscope's tip, and a working channel through which instruments, e.g., diagnostic instruments such as biopsy tools, therapeutic instruments can be inserted.

Bronchoscopes, however, are limited in how far they may be advanced through the airways due to their size. Where the bronchoscope is too large to reach a target location deep in the lungs a clinician may utilize certain real-time imaging modalities such as fluoroscopy. Fluoroscopic images, while useful present certain drawbacks for navigation as it is often difficult to distinguish luminal passageways from solid tissue. Moreover, the images generated by the fluoroscope are two-dimensional whereas navigating the airways of a patient requires the ability to maneuver in three dimensions.

To address these issues, systems have been developed that enable the development of three-dimensional models of the airways or other luminal networks, typically from a series of computed tomography (CT) images. One such system has been developed as part of the ILOGIC® ELECTROMAGNETIC NAVIGATION BRONCHOSCOPY® (ENB™), system currently sold by Covidien LP. The details of such a system are described in commonly assigned U.S. Pat. No. 7,233,820, entitled ENDOSCOPE STRUCTURES AND TECHNIQUES FOR NAVIGATING TO A TARGET IN BRANCHED STRUCTURE, filed on Mar. 29, 2004, by Gilboa, the entire contents of which are incorporated herein by reference.

While the system as described in U.S. Pat. No. 7,233,820 is quite capable, there is always a need for development of improvements and additions to such systems.

SUMMARY

Provided in accordance with the present disclosure is a method of registering a luminal network to a 3D model of the luminal network with real-time feedback.

In an aspect of the present disclosure, the method includes generating the 3D model of the luminal network based on images of the luminal network, generating an electromagnetic field about the luminal network, inserting a location sensor into the electromagnetic field, tracking the location of the sensor within the luminal network, comparing the tracked locations of the sensor with sensors located outside of the luminal network and the portions of the 3D model representative of open space, and presenting on a user interface an indication of which portions of the luminal network have been sufficiently traversed by the sensor to register that portion of the luminal network to the 3D model.

In another aspect of the present disclosure, the method further includes inserting the sensor into a locatable guide.

In a further aspect of the present disclosure, the method further includes inserting the sensor and locatable guide into a bronchoscope.

In yet a further aspect of the present disclosure, the method further includes inserting the bronchoscope into the luminal network, wherein the luminal network is an airway of a patient.

In a further aspect of the present disclosure, the user interface displays a model of the airway.

In a further aspect of the present disclosure, the method further includes presenting on the user interface live bronchoscopic images.

In another aspect of the present disclosure, the live bronchoscopic images depict the sensor as it traverses the luminal network.

In yet another aspect of the present disclosure, the user interface enables the user to end registration.

In another aspect of the present disclosure, the method further includes verifying the registration of the luminal network to the 3D model.

In yet another aspect of the present disclosure, the method further includes presenting on the user interface a 2D slice of the 3D model.

In another aspect of the present disclosure, the 2D slice displays the location of the sensor.

In a further aspect of the present disclosure, the method further includes moving the sensor, wherein movement of the sensor results in presentation of a 2D slice of the luminal network at the location of the sensor has moved to.

In yet a further aspect of the present disclosure, registration is confirmed when upon movement of the sensor the sensor remains substantially within an identified boundary of the luminal network.

In another aspect of the present disclosure, the method further includes presenting on the user interface the 3D model and the locations of the sensor as it traversed the luminal network.

In a further aspect of the present disclosure, the locations of the sensor during registration are presented.

In yet a further aspect of the present disclosure, the locations of the sensor during a procedure are presented.

In another aspect of the present disclosure, the user interface enables the user to return to registration if it is determined that sufficient sensed locations of the sensor are outside of the 3D model.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein.

DETAILED DESCRIPTION

Figure 1:
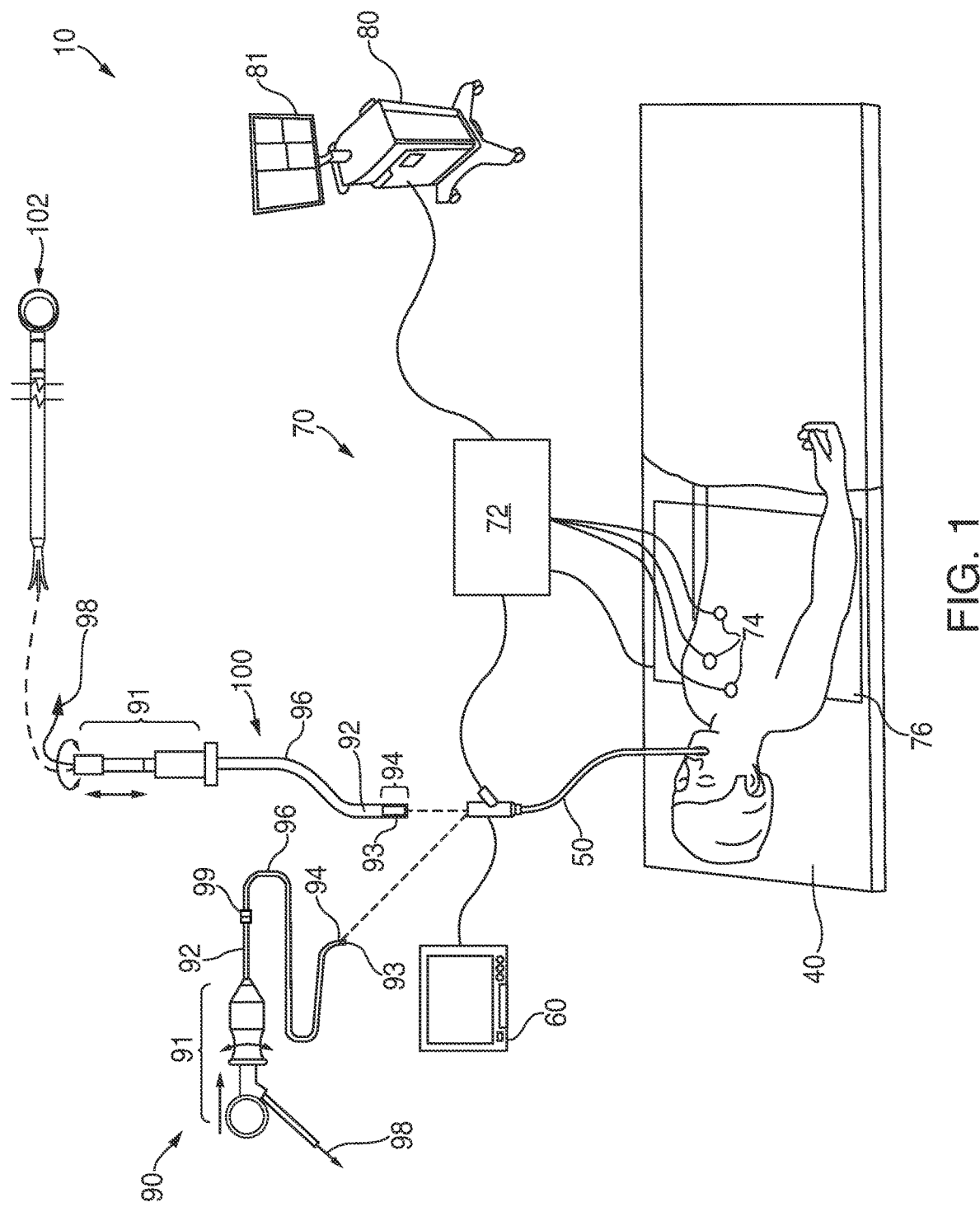
FIG. 1 is a perspective view of an electromagnetic navigation system in accordance with the present disclosure.

The present disclosure is directed to devices, systems, and methods for automatically registering a bronchial tree model with a patient's airways. Various methods for generating the bronchial tree model are envisioned, some of which are more fully described in co-pending U.S. patent application Ser. Nos. 13/838,805, 13/838,997, and 13/839,224, all entitled PATHWAY PLANNING SYSTEM AND METHOD, filed on Mar. 15, 2013, by Baker, the entire contents of all of which are incorporated herein by reference. The registration system of the present disclosure, for example, generally includes at least one sensor whose position is tracked within an electromagnetic field. The location sensor may be incorporated into different types of tools, and enables determination of the current location of the tools within a patient's airways by comparing the sensed location in space to locations within a 3D model of a patients airways. The registration facilitates navigation of the sensor or a tool to a target location and/or manipulation of the sensor or tool relative to the target location. Navigation of the sensor or tool to the target location is more fully described in U.S. Provisional Patent Application No. 62/020,240, entitled SYSTEM AND METHOD FOR NAVIGATING WITHIN THE LUNG, filed on Jul. 2, 2014, by Brown et al., the entire contents of which is incorporated herein by reference.

Additional features of the ENB system of the present disclosure are described in U.S. Provisional Patent Application Nos. 62/020,177, entitled METHODS FOR MARKING BIOPSY LOCATION, filed on Jul. 2, 2014, by Brown; 62/020,238, entitled INTELLIGENT DISPLAY, filed on Jul. 2, 2014, by KEHAT et al.; 62/020,242, entitled UNIFIED COORDINATE SYSTEM FOR MULTIPLE CT SCANS OF PATIENT LUNGS, filed on Jul. 2, 2014, by Greenburg; 62/020,245, entitled ALIGNMENT CT, filed on Jul. 2, 2014, by Klein et al.; 62/020,250, entitled ALGORITHM FOR FLUOROSCOPIC POSE ESTIMATION, filed on Jul. 2, 2014, by Merlet; 62/020,253, entitled TRACHEA MARKING, filed on Jul. 2, 2014, by Lachmanovich et al.; 62/020,257, entitled AUTOMATIC DETECTION OF HUMAN LUNG TRACHEA, filed on Jul. 2, 2014, by Markov et al.; 62/020,261, entitled LUNG AND PLEURA SEGMENTATION, filed on Jul. 2, 2014, by Markov et al.; 62/020,258, entitled CONE VIEW—A METHOD OF PROVIDING DISTANCE AND ORIENTATION FEEDBACK WHILE NAVIGATING IN 3D, filed on Jul. 2, 2014, by Lachmanovich et al.; 62/020,262, entitled DYNAMIC 3D LUNG MAP VIEW FOR TOOL NAVIGATION INSIDE THE LUNG, filed on Jul. 2, 2014, by Weingarten et al.; and U.S. patent application Ser. No. 12/780,678, entitled AUTOMATIC REGISTRATION TECHNIQUE, filed on May 14, 2010, by Dorian Averbuch, the entire contents of all of which are incorporated herein by reference.

Detailed embodiments of such devices, systems incorporating such devices, and methods using the same are described below. However, these detailed embodiments are merely examples of the disclosure, which may be embodied in various forms. Therefore, specific structural and functional details disclosed herein are not to be interpreted as limiting but merely as a basis for the claims and as a representative basis for allowing one skilled in the art to variously employ the present disclosure in virtually any appropriately detailed structure. While the example embodiments described below are directed to the bronchoscopy of a patient's airways, those skilled in the art will realize that the same or similar devices, systems, and methods may also be used in other lumen networks, such as, for example, the vascular, lymphatic, and/or gastrointestinal networks.

With reference to FIG. 1, an electromagnetic navigation (EMN) system 10 is provided in accordance with the present disclosure. One such EMN system is the ELECTROMAGNETIC NAVIGATION BRONCHOSCOPY® system currently sold by Covidien LP. Among other tasks that may be performed using the EMN system 10 are planning a pathway to target tissue, navigating a positioning assembly to the target tissue, navigating a biopsy tool to the target tissue to obtain a tissue sample from the target tissue using the biopsy tool, digitally marking the location where the tissue sample was obtained, and placing one or more echogenic markers at or around the target.

EMN system 10 generally includes an operating table 40 configured to support a patient; a bronchoscope 50 configured for insertion through the patient's mouth and/or nose into the patient's airways; monitoring equipment 60 coupled to bronchoscope 50 for displaying video images received from bronchoscope 50; a tracking system 70 including a tracking module 72, a plurality of reference sensors 74, and an electromagnetic field generator 76; a workstation 80 including software and/or hardware used to facilitate pathway planning, identification of target tissue, navigation to target tissue, and digitally marking the biopsy location FIG. 1 also depicts two types of catheter guide assemblies 90, 100. Both catheter guide assemblies 90, 100 are usable with EMN system 10 and share a number of common components. Each catheter guide assembly 90, 100 includes a handle 91, which is connected to an extended working channel (EWC) 96. EWC 96 is sized for placement into the working channel of a bronchoscope 50. In operation, a locatable guide (LG) 92, including an electromagnetic (EM) sensor 94, is inserted into EWC 96 and locked into position such that EM sensor 94 extends a desired distance beyond a distal tip 93 of EWC 96. The location of EM sensor 94, and thus the distal end of EWC 96, within an electromagnetic field generated by electromagnetic field generator 76 can be derived by tracking module 72, and workstation 80. Catheter guide assemblies 90, 100 have different operating mechanisms, but each contain a handle 91 that can be manipulated by rotation and compression to steer distal tip 93 of LG 92 and EWC 96. Catheter guide assemblies 90 are currently marketed and sold by Covidien LP under the name SUPERDIMENSION® Procedure Kits. Similarly, catheter guide assemblies 100 are currently sold by Covidien LP under the name EDGE™ Procedure Kits. Both kits include a handle 91, EWC 96, and LG 92. For a more detailed description of the catheter guide assemblies 90, 100, reference is made to commonly-owned U.S. patent application Ser. No. 13/836,203 entitled MICROWAVE ABLATION CATHETER AND METHOD OF UTILIZING THE SAME, filed on Mar. 15, 2013, by Ladtkow et al., the entire contents of which are hereby incorporated by reference.

As illustrated in FIG. 1, the patient is shown lying on operating table 40 with bronchoscope 50 inserted through the patient's mouth and into the patient's airways. Bronchoscope 50 includes a source of illumination and a video imaging system (not explicitly shown) and is coupled to monitoring equipment 60, e.g., a video display, for displaying the video images received from the video imaging system of bronchoscope 50.

Catheter guide assemblies 90, 100 including LG 92 and EWC 96 are configured for insertion through a working channel of bronchoscope 50 into the patient's airways (although the catheter guide assemblies 90, 100 may alternatively be used without bronchoscope 50). LG 92 and EWC 96 are selectively lockable relative to one another via a locking mechanism 99. A six degrees-of-freedom electromagnetic tracking system 70, e.g., similar to those disclosed in U.S. Pat. No. 6,188,355 and published PCT Application Nos. WO 00/10456 and WO 01/67035, the entire contents of each of which is incorporated herein by reference, or any other suitable positioning measuring system, is utilized for performing navigation, although other configurations are also contemplated. Tracking system 70 is configured for use with catheter guide assemblies 90, 100 to track the position of EM sensor 94 as it moves in conjunction with EWC 96 through the airways of the patient, as detailed below.

As shown in FIG. 1, electromagnetic field generator 76 is positioned beneath the patient. Electromagnetic field generator 76 and the plurality of reference sensors 74 are interconnected with tracking module 72, which derives the location of each reference sensor 74. One or more of reference sensors 74 are attached to the chest of the patient. The coordinates of reference sensors 74 are sent to workstation 80, which includes and application 81 which uses data collected by sensors 74 to calculate a patient coordinate frame of reference.

Also shown in FIG. 1 is a catheter biopsy tool 102 that is insertable into catheter guide assemblies 90, 100 following navigation to a target and removal of LG 92. Biopsy tool 102 is used to collect one or more tissue samples from the target tissue. As detailed below, biopsy tool 102 is further configured for use in conjunction with tracking system 70 to facilitate navigation of biopsy tool 102 to the target tissue, tracking of a location of biopsy tool 102 as it is manipulated relative to the target tissue to obtain the tissue sample, and/or marking the location where the tissue sample was obtained.

Although navigation is detailed above with respect to EM sensor 94 being included in LG 92 it is also envisioned that EM sensor 94 may be embedded or incorporated within biopsy tool 102 where biopsy tool 102 may alternatively be utilized for navigation without need of LG 92 or the necessary tool exchanges that use of LG 92 requires. A variety of useable biopsy tools are described in U.S. Provisional Patent Application Nos. 61/906,732 and 61/906,762 both entitled DEVICES, SYSTEMS, AND METHODS FOR NAVIGATING A BIOPSY TOOL TO A TARGET LOCATION AND OBTAINING A TISSUE SAMPLE USING THE SAME, filed Nov. 20, 2013 and U.S. Provisional Patent Application No. 61/955,407 having the same title and filed Mar. 14, 2014, the entire contents of each of which is incorporated herein by reference and useable with EMN system 10 as described herein.

During procedure planning, workstation 80 utilizes computed tomographic (CT) image data for generating and viewing the 3D model of the patient's airways, enables the identification of target tissue on the 3D model (automatically, semi-automatically or manually), and allows for the selection of a pathway through the patient's airways to the target tissue. More specifically, the CT scans are processed and assembled into a 3D volume, which is then utilized to generate the 3D model of the patient's airways. The 3D model may be presented on a display monitor associated with workstation 80, or in any other suitable fashion. Using workstation 80, various slices of the 3D volume and views of the 3D model may be presented and/or may be manipulated by a clinician to facilitate identification of a target and selection of a suitable pathway through the patient's airways to access the target. The 3D model may also show marks of the locations where previous biopsies were performed, including the dates, times, and other identifying information regarding the tissue samples obtained. These marks may also be selected as the target to which a pathway can be planned. Once selected, the pathway is saved for use during the navigation procedure. An example of a suitable pathway planning system and method is described in U.S. patent application Ser. Nos. 13/838,805; 13/838,997; and 13/839,224, all entitled PATHWAY PLANNING SYSTEM AND METHOD, filed on Mar. 15, 2014, by Baker, the entire contents of each of which is incorporated herein by reference.

During navigation, EM sensor 94, in conjunction with tracking system 70, enables tracking of EM sensor 94 and/or biopsy tool 102 as EM sensor 94 or biopsy tool 102 is advanced through the patient's airways.

Figure 2:
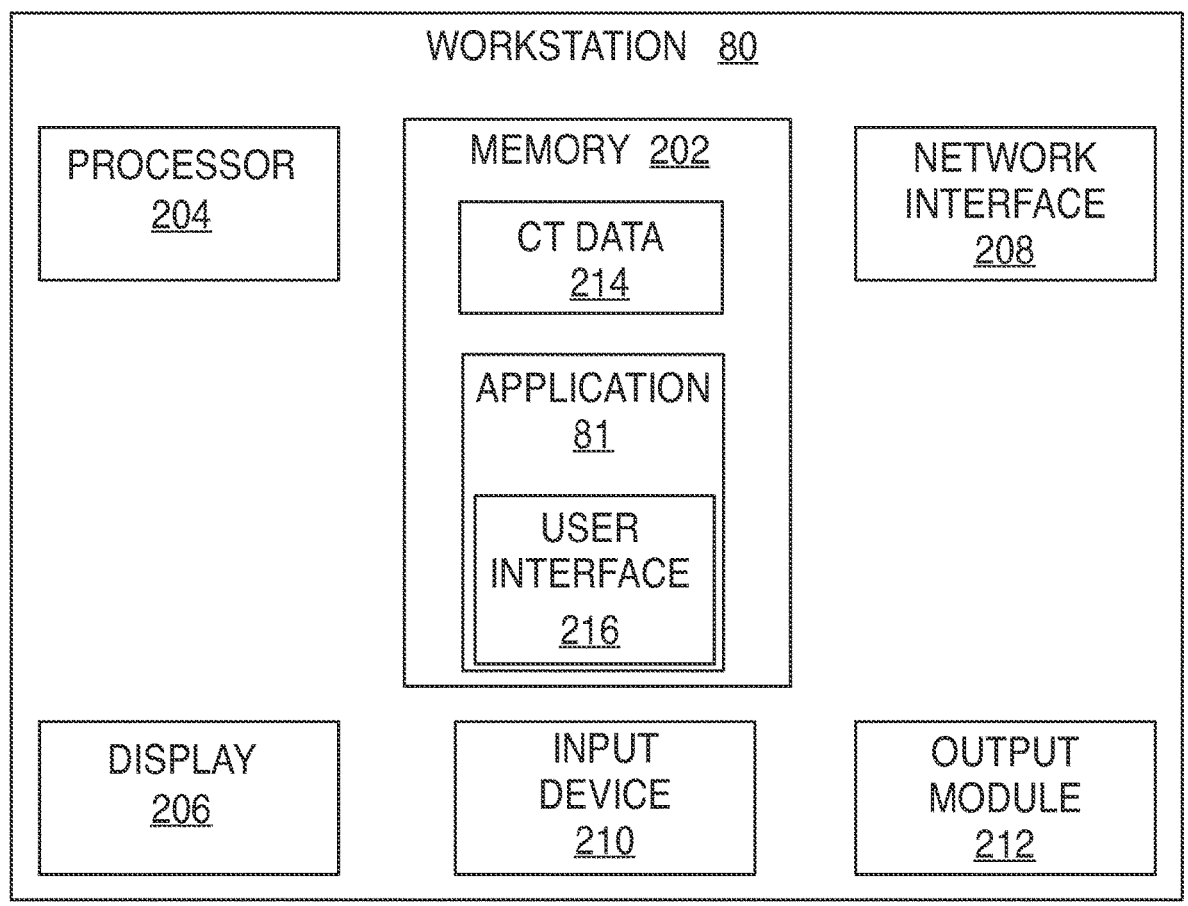
FIG. 2 is a schematic diagram of a workstation configured for use with the system of FIG. 1.

Turning now to FIG. 2, there is shown a system diagram of workstation 80. Workstation 80 may include memory 202, processor 204, display 206, network interface 208, input device 210, and/or output module 212.

Memory 202 includes any non-transitory computer-readable storage media for storing data and/or software that is executable by processor 204 and which controls the operation of workstation 80. In an embodiment, memory 202 may include one or more solid-state storage devices such as flash memory chips. Alternatively or in addition to the one or more solid-state storage devices, memory 202 may include one or more mass storage devices connected to the processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 204. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by workstation 80.

Memory 202 may store application 81 and/or CT data 214. Application 81 may, when executed by processor 204, cause display 206 to present user interface 216. Network interface 208 may be configured to connect to a network such as a local area network (LAN) consisting of a wired network and/or a wireless network, a wide area network (WAN), a wireless mobile network, a Bluetooth network, and/or the internet. Input device 210 may be any device by means of which a user may interact with workstation 80, such as, for example, a mouse, keyboard, foot pedal, touch screen, and/or voice interface. Output module 212 may include any connectivity port or bus, such as, for example, parallel ports, serial ports, universal serial busses (USB), or any other similar connectivity port known to those skilled in the art.

Figure 3A:
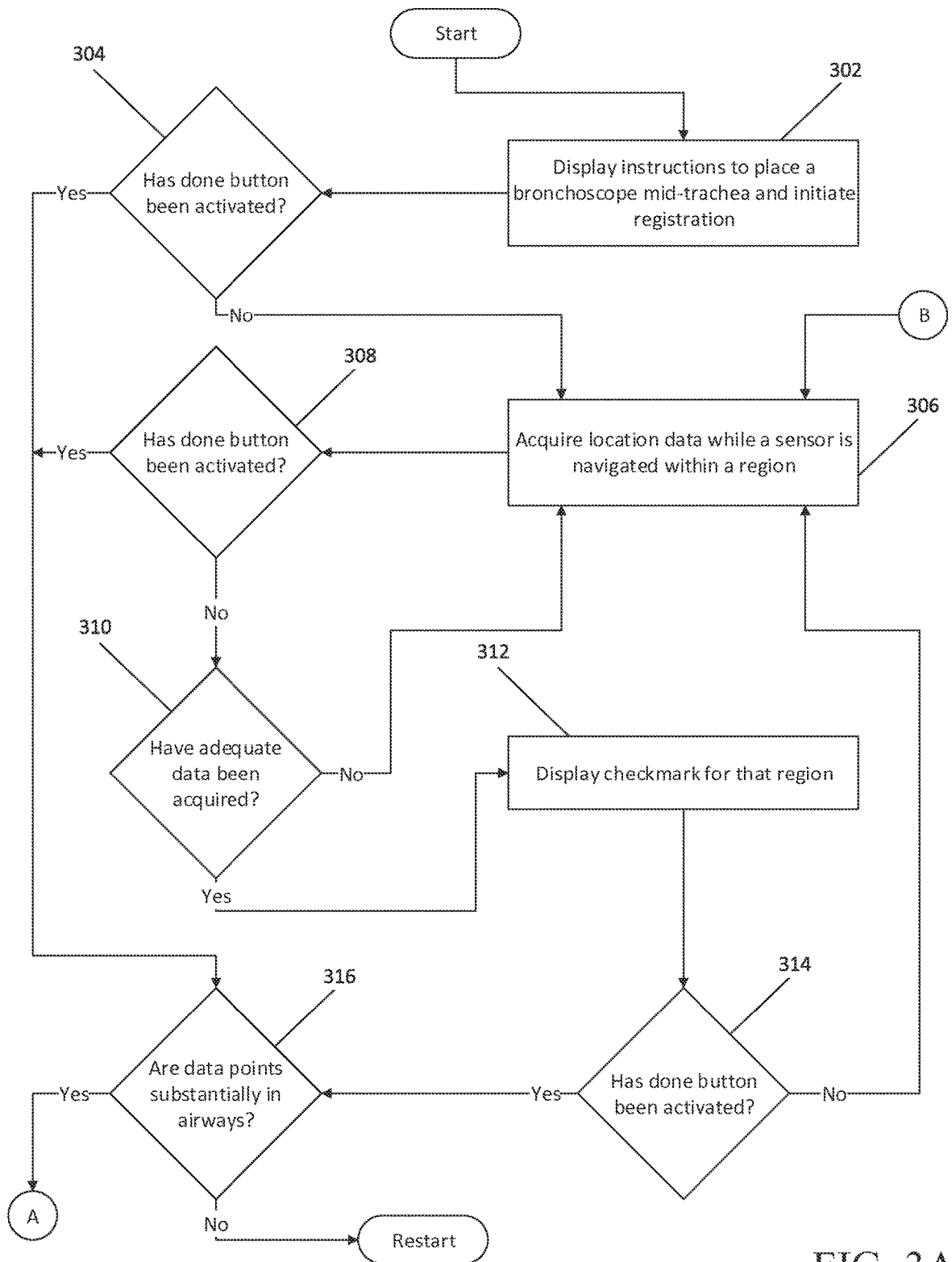
FIGS. 3A and B illustrate a flowchart illustrating a method of registering a luminal network to a 3D model of the luminal network with real-time feedback provided in accordance with the present disclosure.
Figure 3B:
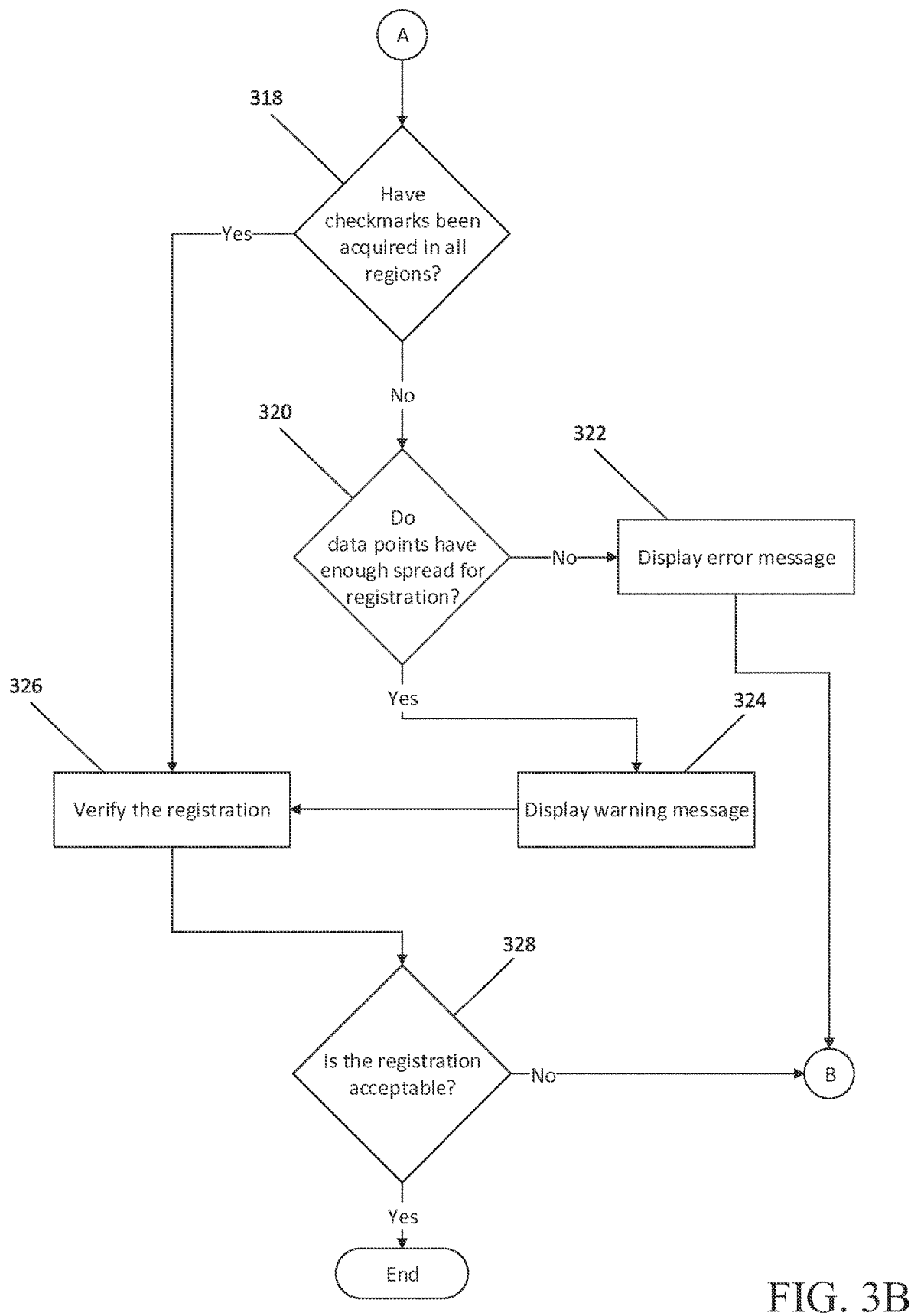

Referring now to FIGS. 3A and B, there is shown a flowchart of an example method for automatically registering the 3D model with a patient's airways. The registration process generally involves the clinician navigating EM sensor 94 through the airways of the patient's lungs to acquire location data. The location data is then compared to the 3D model to register the 3D model with the patient's airways. More specifically, data pertaining to locations of EM sensor 94 while LG 92 is moving through the airways is recorded using electromagnetic field generator 76, reference sensors 74, and tracking module 72. A shape resulting from this location data is compared to an interior geometry of passages of the 3D model, and a location correlation between the shape and the 3D model based on the comparison is determined, e.g., utilizing application 81. In addition, application 81 identifies non-tissue space (e.g., air filled cavities) in the 3D model. Application 81 aligns, or registers, an image representing a location of EM sensor 94 of LG 92 with an image of the 3D model based on the recorded location data and an assumption that LG 92 remains located in non-tissue space in the patient's airways. Tracking system 70 tracks the location of LG 92 via EM sensor 94 as LG 92 is navigated through the patient's airways. Tracking the location of LG 92 inside the patient's airways allows application 81 to register the bronchial tree model with the patient's airways. Prior to the start of registration, the clinician loads a navigation plan into application 81 from memory 202, a USB device, or from network interface 208. The navigation plan may require that all or only some regions of the patient's lungs be registered.

At step 302, user interface 216 displays instructions for a clinician performing registration to insert bronchoscope 50 into the patient via the patient's mouth or nose, and to place bronchoscope 50 mid-trachea in the patient. Next, the clinician inserts LG 92 into EWC 96, and the combination into bronchoscope 50 such that EM sensor 94 projects out from the distal end of bronchoscope 50 by, for example, 10 mm. LG 92 and EWC 96 are locked in place such that they move in concert with one another. Alternatively, EM sensor 94 may be embedded within the distal tip of EWC 96 and operate independently of LG 92.

Figure 4:
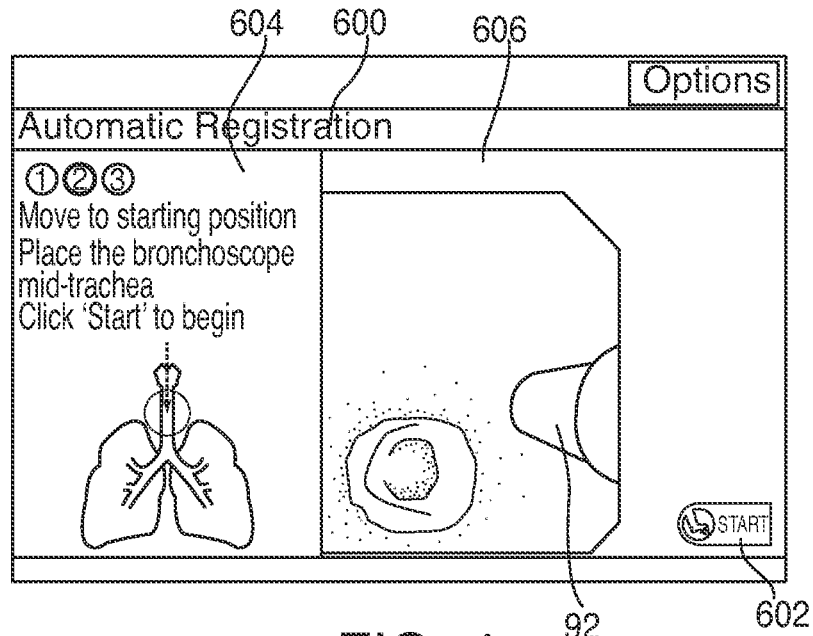
FIG. 4 shows a lung survey prior to the start of registration.
Figure 5:
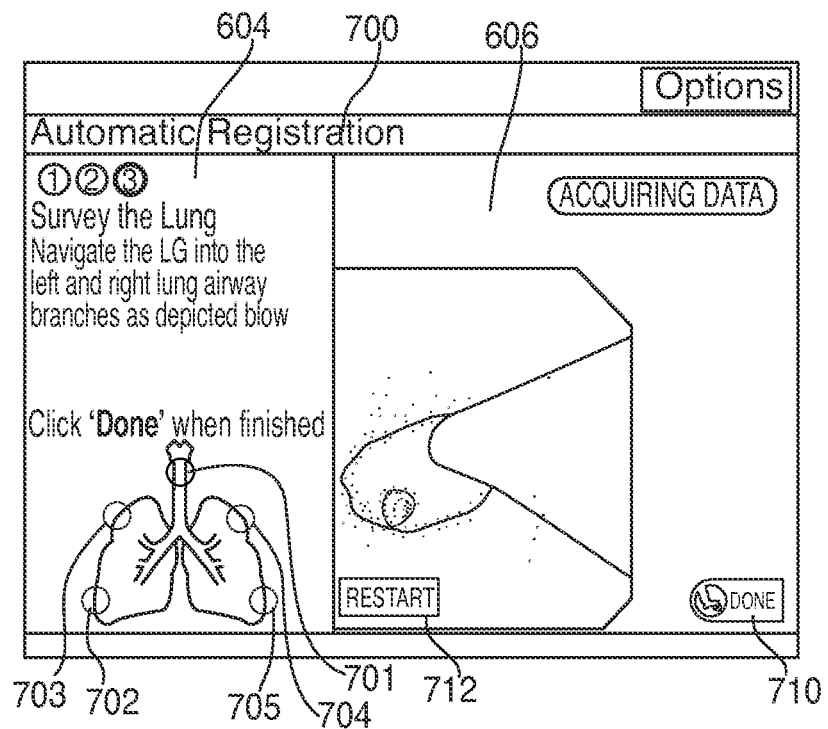
FIG. 5 shows the lung survey of FIG. 4 after registration has started.

These instructions may be presented to the clinician via a view 600 including a lung survey progression indicator 604 and a video feed 606, as shown in FIG. 4. Lung survey progression indicator 604 may provide the clinician with instructions on how to perform registration. Video feed 606 may present a real-time video feed captured by the video imaging system of bronchoscope 50. When the clinician is ready to start registration, the clinician may activate a "start" button 602 in user interface 216. The clinician may activate "start" button 602 by, for example, using a mouse or foot pedal, or by giving a voice command. When "start" button 602 is activated, user interface 216 may present a view 700 wherein lung survey progression indicator 604 shows the regions of the patient's lungs to be registered, as shown in FIG. 5. The regions of the patient's lungs may correspond to the patient's lung lobes, and may include regions 701, 702, 703, 704, and/or 705. Alternatively, the regions may correspond to other sub-regions of a lung or of a particular lobe of a lung. In the embodiment shown in FIG. 5, the navigation plan calls for only 4 regions as well as the trachea to be registered, thus a total of 5 regions, but not necessarily all 5 lobes. One of skill in the art will recognize that a survey of all five lobes of the lungs will provide more data and potentially better registration. But as detailed below, such specificity is not necessarily required to achieve adequate registration of the CT images and the bronchial tree model formed therefrom to the patient's anatomy. View 700 also includes a "done" button 710 which the clinician may activate at any time to end the data acquisition phase of the registration process, and a "restart" button 712 which the clinician may activate at any time in order to restart the registration.

At step 304, application 81 determines whether "done" button 710 has been activated. If "done" button 710 has been activated, processing proceeds to step 316. If "done" button 710 has not been activated, processing proceeds to step 306 where application 81 acquires location data while the clinician navigates EM sensor 94 about the patient's lungs. The clinician may navigate EM sensor 94 through the patient's airways into a first region of the patient's lungs. The clinician may choose to acquire location data in any lung region and in any order during the data acquisition portion of the registration process. EM sensor 94 may be navigated down multiple branches of the airways in the first region of the patient's lungs to acquire location data spread throughout the lung region. By acquiring location data in various branches of the airways spread throughout the lung region, application 81 may generate a more accurate shape to correlate with the 3D model. Further, by acquiring location data with sufficient depth, that is, by navigating EM sensor 94 deep enough into the airways, the accuracy of the shape may further be improved. For example, application 81 may require EM sensor 94 to be navigated to the second bifurcation of each airway passage of a lung region to acquire sufficient location data and depth of penetration before determining that that region has been sufficiently surveyed. The clinician receives feedback from application 81 in the form of a checkmark in that region on the survey progression indicator 604 signifying that sufficient data has been acquired and at a sufficient depth of penetration.

While performing the data acquisition step 306, the application 81 may periodically execute step 308, where application 81 again determines whether "done" button 710 has been activated. If "done" button 710 has been activated, processing proceeds to step 316. If "done" button 710 has not been activated, processing proceeds to step 310, where application 81 determines whether adequate location data have been collected. This determination may be composed of two steps. First, application 81 may determine whether enough data points have been acquired to even start registration processing. If enough data points have been acquired, application 81 may perform a second step of determining whether the survey has reached sufficient depth in a particular region. If application 81 determines that adequate data have been collected and sufficient depth of survey has been achieved, user interface 216 may provide the checkmark feedback in lung survey progression indicator 604 to the clinician, as described above. For example, application 81 may require that at least 200 data points be acquired for each lung region and to a sufficiency of depth. Having too few data points, or having the data points concentrated too shallow in the lung region may result in the location data being insufficient to provide the feedback to the clinician.

Figure 6:
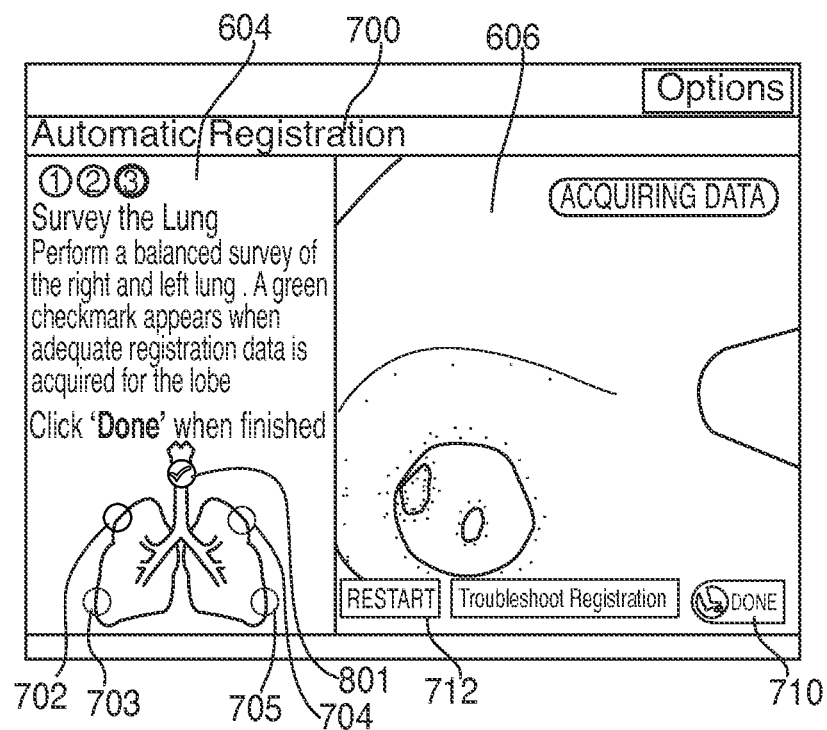
FIG. 6 shows the lung survey of FIG. 5 with an indicator activated for the trachea.
Figure 7:
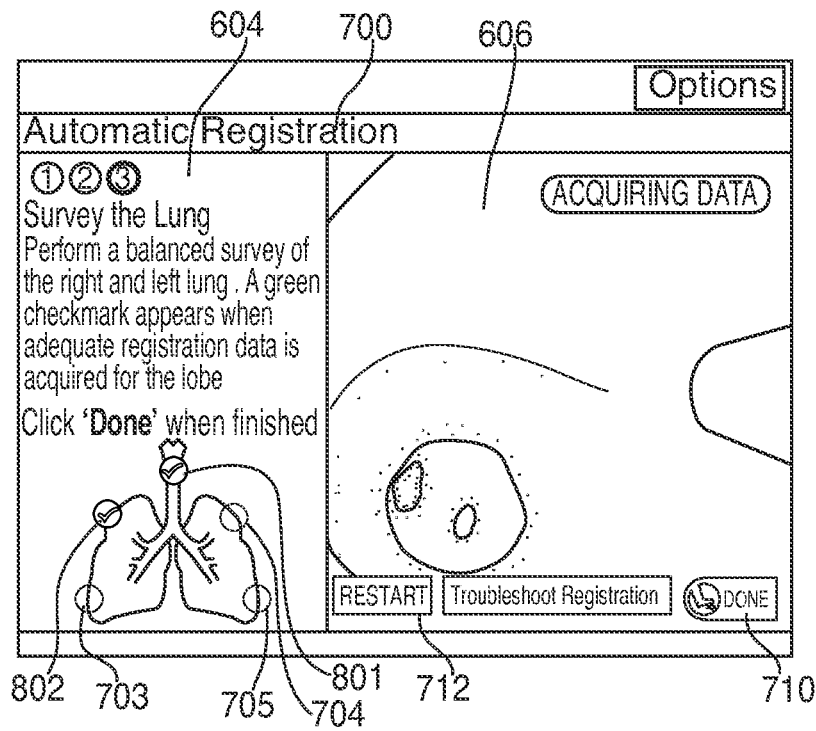
FIG. 7 shows the lung survey of FIG. 6 with an additional indicator activated for a first region of the lung.
Figure 8:
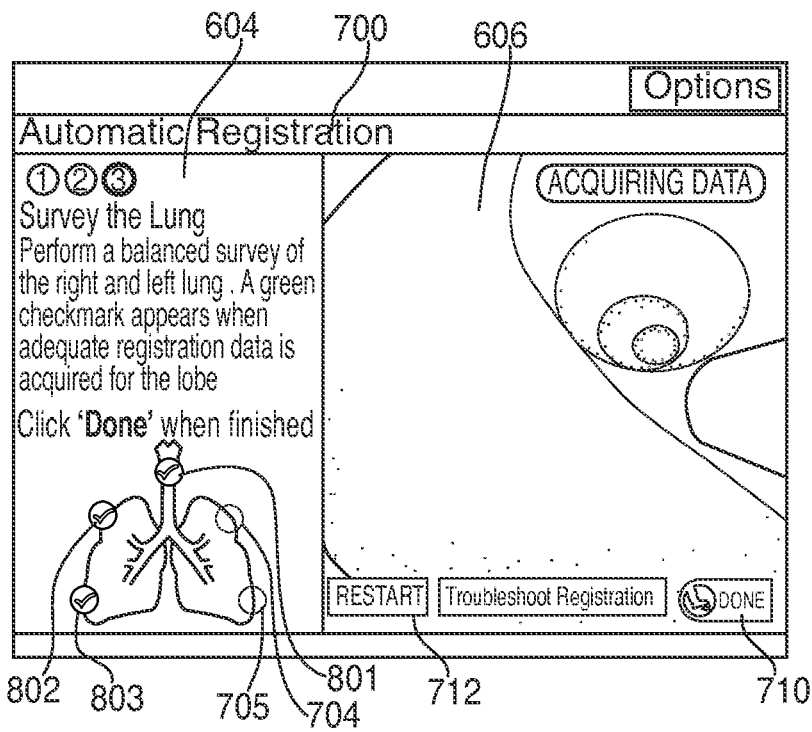
FIG. 8 shows the lung survey of FIG. 7 with an additional indicator activated for a second region of the lung.
Figure 9:
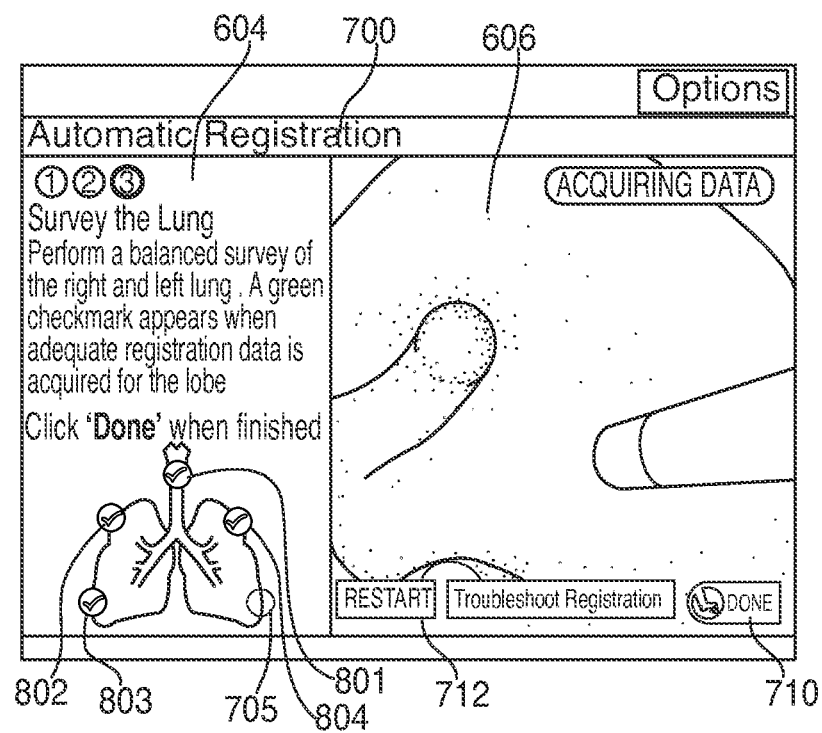
FIG. 9 shows the lung survey of FIG. 8 with an additional indicator activated for a third region of the lung.
Figure 10:
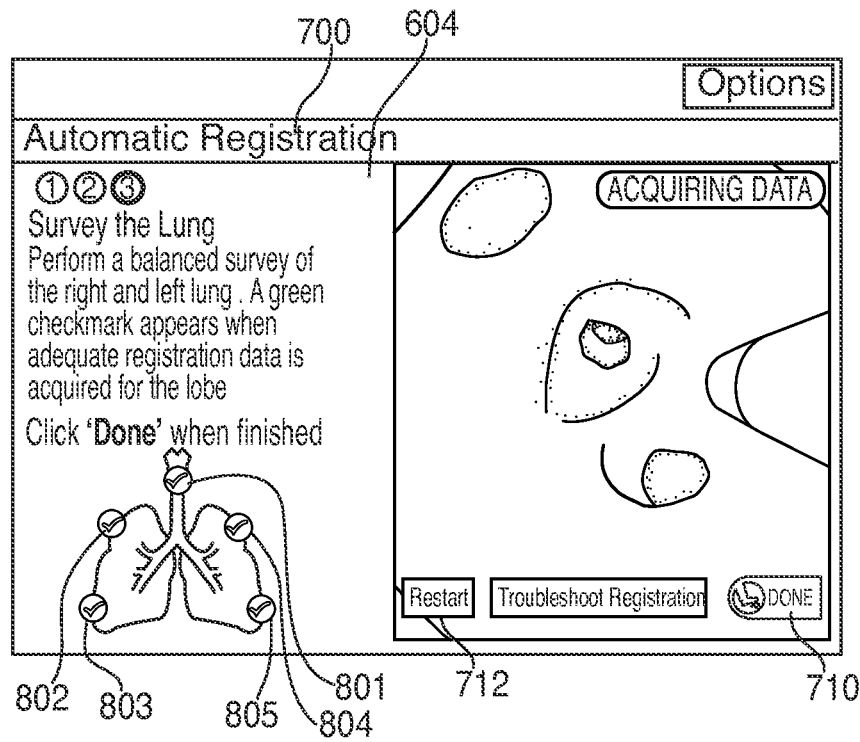
FIG. 10 shows the lung survey of FIG. 9 with an additional indicator activated for a fourth region of the lung.

If application 81 determines that the acquired location data is inadequate, processing returns to step 306, where more location data is acquired. If application 81 determines that the acquired location data is sufficient, processing proceeds to step 312, where user interface 216 updates view 700 to display a feedback indicator 801, such as a "check mark" symbol, indicating that a particular lung region has been sufficiently surveyed, as shown in FIG. 6. FIGS. 6-10 show successive updates to view 700 as the location data acquisition phase progresses with each of lung regions 701, 702, 703, 704, and/or 705 being indicated as having adequate data acquired with feedback indicators 801, 802, 803, 804, and/or 805.

Thereafter, at step 314, application 81 again determines whether "done" button 710 has been activated. If "done" button 710 has not been activated, processing loops back to step 306. If "done" button 710 has been activated, processing proceeds to step 316, where application 81 determines whether the acquired data points are located substantially within the airways of the corresponding 3D model. If the acquired data points are not substantially located within the airways, the data acquisition phase of registration has been unsuccessful and the entire process must be restarted. If the acquired data points are located substantially within the airways, processing proceeds to step 318.

At step 318, application 312 determines whether all lung regions have received "check marks" and thus have been adequately surveyed. If yes, processing proceeds to step 326. If not, processing proceeds to step 320, where application 81 determines whether the data points that have been acquired are distributed through the lung regions with enough spread to be sufficient for registration. While in a preferred embodiment the clinician will continue to acquire location data until all regions have received "check marks," it is possible to end the location data acquisition phase of the registration process at any time by activating the "done" button, which will then cause application 81 to analyze the acquired location data to determine whether registration is possible based on the acquired data points.

If the acquired data points are not distributed through the lung regions with enough spread, processing proceeds to step 322, where user interface 216 displays an error message, where after processing returns to step 306 signifying to the clinician that insufficient data, insufficient spread of data, or insufficient depth of penetration have resulted in insufficient data collection for registration. If application 81 determines that the acquired data points are distributed through the lung regions with enough spread for registration, processing proceeds to step 324 where user interface 216 displays a message warning the clinician that, even though it is possible to perform registration based on the acquired location data, it is not ideal and the registration could be improved by acquiring additional location data.

Figure 11:
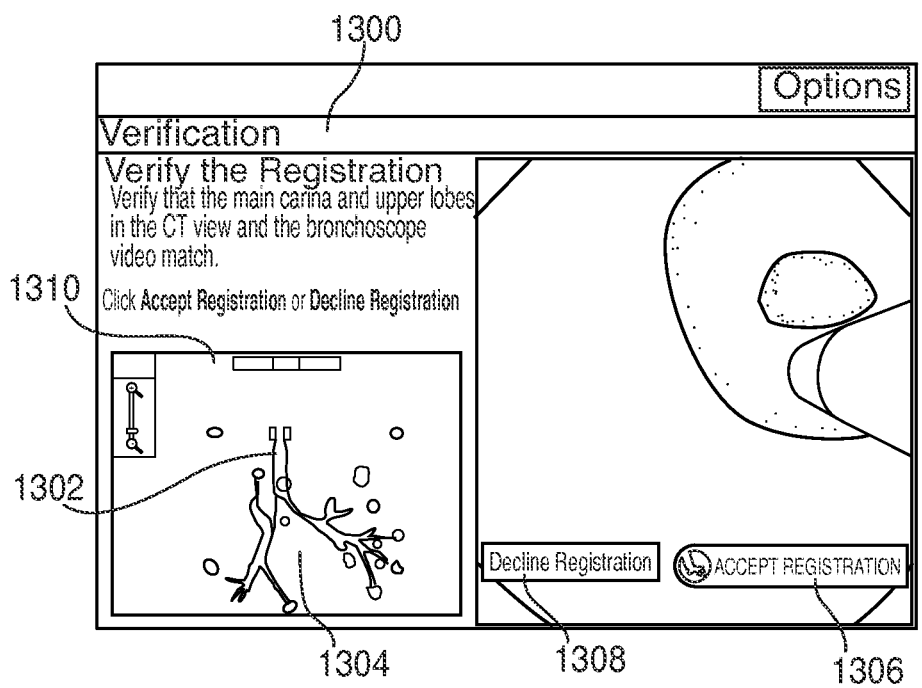
FIG. 11 shows a view presenting a slice of a 3D volume for verifying registration in accordance with an embodiment of the present disclosure.
Figure 12:
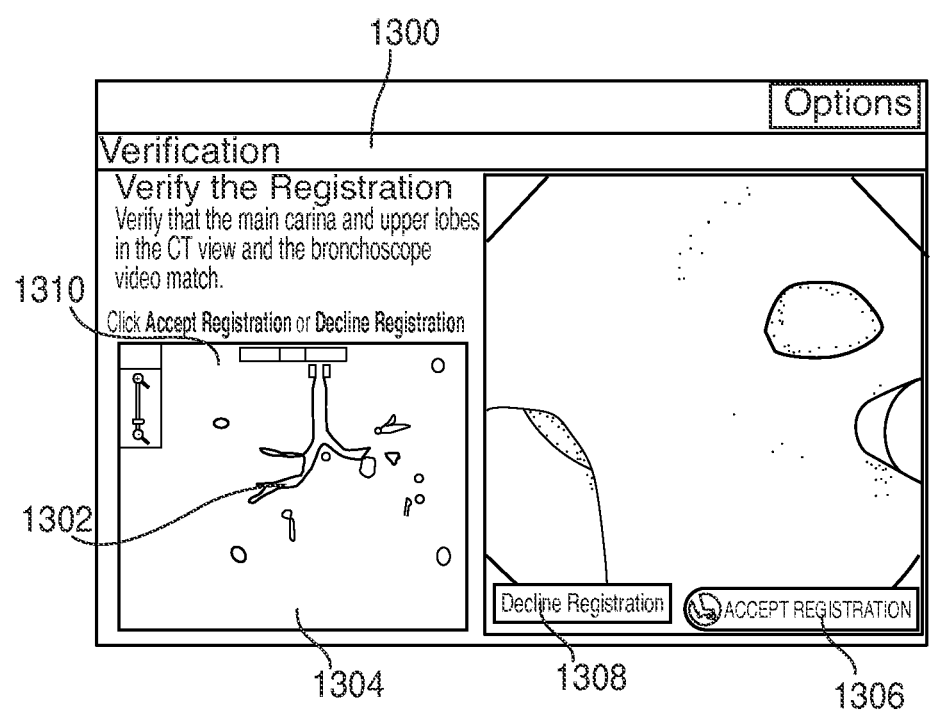
FIG. 12 shows the view of FIG. 11, presenting a further slice for verifying registration following movement of a sensor.
Figure 13:
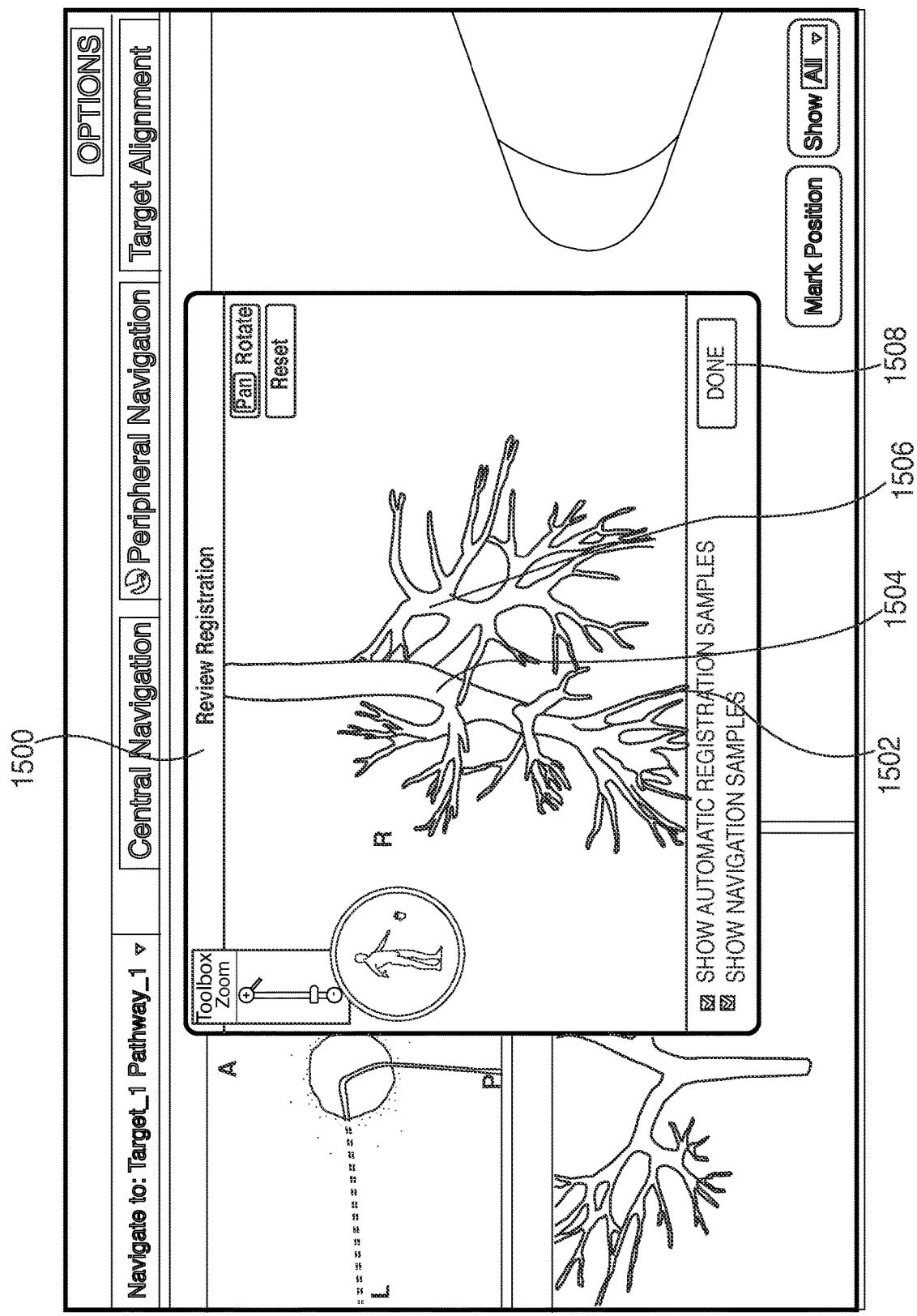
FIG. 13 shows a view for reviewing the registration in a 3D model in accordance with an embodiment of the present disclosure.

Thereafter, processing proceeds to step 326 where user interface 216 presents the clinician with a view 1300 for registration verification as shown in FIG. 11. View 1300 presents the clinician with a stationary EM sensor indicator 1302 overlaid on a displayed slice 1304 of the 3D volume of the currently loaded navigation plan, for example, as shown in FIG. 13. The displayed slice 1304 may move about the EM sensor indicator 1302, and a different slice 1304 of the 3D volume may be displayed as the position of EM sensor 94 within the patient's airways change, with EN sensor indicator 1302 remaining stationary, as can be seen by comparison of FIGS. 11 and 12. Although the slice 1304 displayed in FIG. 11 is from the coronal direction, the clinician may alternatively select one of the axial or sagittal directions by activating a display bar 1310. As the clinician advances EM sensor 94 through the patient's airways, the displayed slice 1304 changes based on the position of EM sensor 94 relative to the registered 3D volume.

At step 328, it is determined whether the registration is acceptable. For example, the clinician may determine whether the registration is acceptable. Once the clinician is satisfied that the registration is acceptable, for example, by determining that the EM sensor indicator 1302 does not stray from within the patient's airways as presented in the displayed slice 1304, the clinician accepts the registration by activating the "accept registration" button 1306. However, if the clinician determines that the registration is not acceptable, for example, if EM sensor indicator 1302 strays from within the patient's airways as presented in the displayed slice 1304, the clinician may decline the registration by activating the "decline registration" button 1308, and proceed to repeat the registration process starting at step 306. Although registration has now been completed by the clinician, the system 10 may continue to track the location of EM sensor 94 within the patient's airways relative to the 3D volume and may continue to update and improve the registration during a subsequent navigation procedure.

Additionally, the registration of the patient's lungs may be reviewed either before or during navigation. As shown in FIG. 13, application 81 may present a "Review Registration" view 1500 showing the 3D model 1502 with indicators 1504 and 1506 for each location where the location of EM sensor 94 was tracked. Different shaped or colored indicators may be displayed for locations tracked during registration (i.e. indicators 1504) and locations tracked during navigation (i.e. indicators 1506). By using this view, the clinician can be confirm that all tracked locations of EM sensor 94 are located within the 3D model's airways. If the tracked locations of EM sensor 94 are located outside of the 3D model's airways, the registration is either incomplete or incorrect, and can be repeated. The clinician may open view 1500 at any time before or during navigation, and may close the view by activating the "done" button 1508.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of confirming accuracy of registration of a luminal network to a 3D model of the luminal network, the method comprising:
generating the 3D model of a luminal network based on a plurality of 2D slice images of the luminal network;
generating, by an electromagnetic (EM) field generator, an EM field about the luminal network;
inserting an EM sensor into the luminal network;

obtaining data points corresponding to tracked locations of the EM sensor by tracking the EM sensor within the luminal network;

comparing the data points with the 3D model;

registering at least one of a plurality of discrete regions of the 3D model with the luminal network based on the comparing;

presenting, on a user interface an indication of whether the at least one of the plurality of discrete regions of the 3D model is registered with the luminal network;

presenting, on the user interface:
    an airway of the luminal network in a 2D slice image of the plurality of 2D slice images; and
    an EM sensor indicator corresponding to the tracked locations of the EM sensor within the luminal network on the presented 2D slice image relative to the airway of the luminal network in the 2D slice image;

processing an input declining registration of the luminal network to the 3D model when the EM sensor indicator is presented outside the airway of the luminal network in the 2D slice image; and confirming registration of the luminal network to the 3D model when the EM sensor indicator is presented inside the airway of the luminal network in the 2D slice image.

2. The method of claim 1, wherein the user interface displays a 3D model of the airway.

3. The method of claim 1, further comprising presenting, on the user interface, live bronchoscopic images separate from the presented 2D slice image.

4. The method of claim 3, wherein the live bronchoscopic images depict the EM sensor as it traverses the luminal network.

5. The method of claim 1, wherein the user interface enables a user to end registration.

6. The method of claim 1, further comprising moving the EM sensor, wherein movement of the EM sensor results in presentation of a new 2D slice image of the plurality of 2D slice images at a location to which the EM sensor has moved, wherein the new 2D slice image is different from the presented 2D slice image.

7. The method of claim 6, wherein registration is confirmed when, upon movement of the EM sensor, the EM sensor remains within an identified boundary of the luminal network presented on the new 2D slice image.

8. The method of claim 1, further comprising presenting, on the user interface, a rendering of the 3D model and EM sensor indicators corresponding to the tracked locations of the EM sensor as it traverses the luminal network on the presented rendering of the 3D model.

9. The method of claim 8, wherein the user interface enables a user to return to registration if it is determined that sensed locations of the EM sensor are outside of the rendering of the 3D model.

10. The method of claim 1, wherein the luminal network includes a plurality of regions, and wherein obtaining data points includes obtaining data points to a second bifurcation of each region of the luminal network.

11. The method of claim 1, wherein the indication is a check mark for the discrete region.

12. A method of confirming accuracy of registration of a luminal network to a 3D model of the luminal network, the method comprising:
    generating the 3D model of a luminal network based on a plurality of 2D slice images of the luminal network;
    generating, by an electromagnetic (EM) field generator, an EM field about the luminal network;
    obtaining data points corresponding to tracked locations of an EM sensor by tracking the EM sensor within the luminal network;
    comparing the data points with the 3D model;
    registering at least one of a plurality of discrete regions of the 3D model with the luminal network based on the comparing;
    presenting, on a user interface:
        an airway of the luminal network in a 2D slice image of the plurality of 2D slice images; and
        an EM sensor indicator corresponding to the tracked locations of the EM sensor within the luminal network on the presented 2D slice image relative to the airway of the luminal network in the 2D slice image;
    processing an input declining the registration of the luminal network to the 3D model when the EM sensor indicator is presented outside the airway of the luminal network in the 2D slice image; and
    confirming registration of the luminal network to the 3D model when the EM sensor indicator is presented inside the airway of the luminal network in the 2D slice image, wherein the presented 2D slice image is fixed in position and movement of the EM sensor results in movement of the EM sensor indicator.

13. The method of claim 12, wherein the EM sensor indicator is fixed in position and movement of the EM sensor results in presentation of a new 2D slice image of the plurality of 2D slices images at a location to which the EM sensor has moved.

14. A method of confirming accuracy of registration of a luminal network to a 3D model of the luminal network, the method comprising:
    generating the 3D model of a luminal network based on a plurality of 2D slice images of the luminal network;
    generating, by an electromagnetic (EM) field generator, an EM field about the luminal network;
    obtaining data points corresponding to tracked locations of an EM sensor by tracking the EM sensor within the luminal network;
    comparing the data points with the 3D model;
    registering at least one of a plurality of discrete regions of the 3D model with the luminal network based on the comparing;
    presenting, on the user interface:
        an airway of the luminal network in a 2D slice image of the plurality of 2D slice images; and
        an EM sensor indicator corresponding to the tracked locations of the EM sensor within the luminal network on the presented 2D slice image relative to the airway of the luminal network in the 2D slice image;
    processing an input declining registration of the luminal network to the 3D model when the EM sensor indicator is presented outside the airway of the luminal network in the 2D slice image; and
    confirming registration of the luminal network to the 3D model when the EM sensor indicator is presented inside the airway of the luminal network in the 2D slice image, wherein the EM sensor indicator is fixed in position and movement of the EM sensor results in presentation of a new 2D slice image of the plurality of 2D slice images at a location to which the EM sensor has moved.

15. The method of claim 14, wherein the presented 2D slice image is fixed in position and movement of the EM sensor results in movement of the EM sensor indicator.

* * * * *